(12) United States Patent
Ihn et al.

(10) Patent No.: US 8,812,251 B2
(45) Date of Patent: Aug. 19, 2014

(54) SYSTEM AND METHOD FOR MONITORING BONDING INTEGRITY

(75) Inventors: Jeong-Beom Ihn, Bellevue, WA (US); Jonathan Henry Gosse, Issaquah, WA (US); Kay Y. Blohowiak, Issaquah, WA (US); William B. H. Grace, Seattle, WA (US)

(73) Assignee: The Boeing Company, Chicago, IL (US)

( * ) Notice: Subject to any disclaimer, the term of this patent is extended or adjusted under 35 U.S.C. 154(b) by 615 days.

(21) Appl. No.: 13/085,450

(22) Filed: Apr. 12, 2011

(65) Prior Publication Data

US 2012/0265449 A1 Oct. 18, 2012

(51) Int. Cl.
| | | |
|---|---|---|
| G01B 3/00 | (2006.01) |
| G01N 27/02 | (2006.01) |
| B29C 65/82 | (2006.01) |
| B29C 65/50 | (2006.01) |
| C09J 5/00 | (2006.01) |
| G01N 27/20 | (2006.01) |
| G01N 3/00 | (2006.01) |
| B64C 1/00 | (2006.01) |
| B29C 65/00 | (2006.01) |
| B29L 31/30 | (2006.01) |
| B29K 105/20 | (2006.01) |
| F16B 11/00 | (2006.01) |

(52) U.S. Cl.
CPC .............. G01N 27/20 (2013.01); G01N 27/026 (2013.01); *B29C 66/73941* (2013.01); *B29C 65/8276* (2013.01); *B29C 66/73921* (2013.01); *B29C 66/7212* (2013.01); *B29C 65/5057* (2013.01); *B29L 2031/3085* (2013.01); *B29K 2105/206* (2013.01); *C09J 5/00* (2013.01); *B29C 66/721* (2013.01); *B29C 65/5021* (2013.01); *B29C 65/8292* (2013.01); *B29L 2031/3082* (2013.01); *B29L 2031/3076* (2013.01); *B29C 66/45* (2013.01); *F16B 11/006* (2013.01); *B29C 65/5028* (2013.01); *G01N 3/00* (2013.01); *B29L 2031/3079* (2013.01); *B64C 1/00* (2013.01)
USPC .................. 702/33; 702/34; 702/57; 702/182

(58) Field of Classification Search
USPC ............... 702/34, 35, 57, 182; 324/71.1, 663; 73/12.09, 801, 802
See application file for complete search history.

(56) References Cited

U.S. PATENT DOCUMENTS

| | | | |
|---|---|---|---|
| 6,384,610 B1 * | 5/2002 | Wilson ......................... 324/663 |
| 7,367,236 B2 * | 5/2008 | Georgeson et al. ............. 73/801 |
| 7,414,416 B2 | 8/2008 | Watkins, Jr. et al. |
| 2007/0166831 A1 | 7/2007 | Watkins, Jr. et al. |
| 2009/0294022 A1 | 12/2009 | Hayes et al. |
| 2010/0005896 A1 | 1/2010 | Miller et al. |

FOREIGN PATENT DOCUMENTS

| | | |
|---|---|---|
| EP | 0573778 A1 | 12/1993 |
| EP | 2070688 A2 | 6/2009 |
| WO | 00/46593 A2 | 8/2000 |
| WO | 03/076953 A2 | 9/2003 |

OTHER PUBLICATIONS

Tom Zhuang, "Design of Smart Adhesive Films for Bondline Integrity Monitoring", Feb. 8, 2012, Structures and Composites Laboratory (SACL) at Stanford University, Palo Alto, California, XP55025731, Retrieved from internet at URL: structure.stanford.edu/documents%5Cprojects%5Czhuang.pdf (retrieved on Jun. 1, 2012), 8 pages.

Alan Wilson et al., "MEMS Adhesive Bond Degradation Sensor", Analatom Inc., Sunnyvale, CA, Aeronautical and Maritime Research Lab, Melbourne, Australia, Dec. 15, 2000, 8 pages.

PCT International Search Report and Written Opinion for counterpart International Application PCT/US2012/024425, Mailed May 10, 2012, 13 pages.

Jeong-Beom Ihn et al., "Detection and monitoring of hidden fatigue crack growth using a built-in piezoelectric sensor/actuator network: I. Diagnostics", Smart Materials and Structures, Institute of Physics Publishing, 13 (2004) pp. 609-620, Printed in the UK.

Jeong-Beom Ihn et al., "Detection and monitoring of hidden fatigue crack growth using a built-in piezoelectric sensor/actuator network: II. Validation using riveted joints and repair patches", Smart Materials and Structures, Institute of Physics Publishing, 13 (2004) pp. 621-630, Printed in the UK.

Jeong-Beom Ihn et al., "Pitch-catch Active Sensing Methods in Structural Health Monitoring for Aircraft Structures", Structural Health Monitoring, SAGE Publications, 2008, vol. 7(1), pp. 5-19.

* cited by examiner

*Primary Examiner* — Elias Desta

(57) ABSTRACT

The disclosure provides in one embodiment a system for monitoring adhesive integrity within a cured bondline of a bonded structural assembly. The system comprises a bonded structural assembly having a cured bondline. The cured bondline comprises an adhesive layer, a scrim ply layer integrated with the adhesive layer, and an electrical sensor network integrated with the scrim ply layer. The system further comprises an electrical power source for providing electrical power to the electrical sensor network. The system further comprises a digital data communications network for retrieving and processing data from the electrical sensor network. The electrical sensor network monitors adhesive integrity on demand by interpreting changes in local dynamic responses and electromechanical properties directly measured within the cured bondline.

20 Claims, 9 Drawing Sheets

SYSTEM AND METHOD FOR MONITORING BONDING INTEGRITY

BACKGROUND

1) Field of the Disclosure

The disclosure relates generally to systems and methods for monitoring bonding integrity, and more particularly, to systems and methods for monitoring adhesive bonding integrity of bonded structural assemblies, such as composite structural assemblies.

2) Description of Related Art

The manufacture and assembly of structures and structural components has increasingly involved the use of bonded joints or bondlines, such as adhesive bonded joints or bondlines, instead of fastener devices, to bond or join the structural components together. Adhesive bonded joints may be used in bonding of composite structural components in combination with other composites or other materials such as metal. In this regard, adhesive bonded composite structures and structural components may typically be used in the manufacture and assembly of aircraft, spacecraft, rotorcraft, watercraft, automobiles, trucks, buses, and other vehicles and structures due to the design flexibility and low weight of such composite structures and structural components.

Known inspection methods and devices exist for assessing the integrity of adhesive bonded joints or bondlines in order to measure the quality, soundness, effectiveness, performance, strength, or other characteristics of the adhesive bond, as well as to assess the ability of the adhesive bond to function reliably as required throughout the predicted lifetime of the bonded structure or structural components. Such known inspection methods and devices may include a variety of time-consuming techniques such as visual inspection, localized non-destructive inspection methods, laser bond and ultrasonic inspection devices, or other known methods and devices. These known inspection methods and devices may require that the hardware be pulled out of service for the inspection and may not have the ability to interrogate the bondline while the component part is in-service. In addition, such inspection methods and devices may increase costs and flow time to the process of assuring bondline integrity. Moreover, such known inspection methods and devices may only be carried out at certain times or on a periodic basis, rather than having the information about the bondline integrity available at all times on demand and available on a continuous, real time basis.

In particular, known visual inspection and localized non-destructive inspection methods and devices may not be effective where visual access to the adhesive bonded joints or bondlines is limited or not possible, for example, if such adhesive bonded joints or bondlines are located in a remote or interior location or beneath the surface. Access to interior bonded joints and bondlines may be difficult or not possible without disassembly or damage to the structures or structural components, such as removing a part or drilling a hole into a structure for insertion of a measurement tool. In addition, ultrasonic inspections may require specialized equipment, substantial operator training, and effective access to the structural component.

In addition, known methods and devices exist for monitoring the health of a composite structure with the use of external sensors. For example, U.S. Patent Publication Number 2007/0166831 A1 to Watkins, Jr. et al., discloses a method for monitoring the health of a composite structure by disposing a condition sensor on the surface of the composite structure. However, positioning sensors on the external surface of the structure may provide measurements of the whole structure including measurements through the structural components and the bondline. Such known methods and devices may provide only indirect and less accurate measurements of bondline characteristics and not direct and more accurate measurements of bondline characteristics at or within the bondline. In addition, alignment and positioning of external sensors may be complicated by accessibility to the structure or structural component, for example, inaccessibility to one side of a composite sandwich structure.

Accordingly, there is a need in the art for an improved system and method for monitoring bonding integrity directly at or within adhesive bonded joints or bondlines of structures or structural assemblies where such improved system and method provide advantages over known systems and methods.

SUMMARY

This need for a system and method for monitoring bonding integrity directly at or within adhesive bonded joints or bondlines of structures or structural assemblies is satisfied. As discussed in the below detailed description, embodiments of the system and method may provide significant advantages over existing systems and methods.

In an embodiment of the disclosure, there is provided a system for monitoring adhesive integrity within a cured bondline of a bonded structural assembly. The system comprises a bonded structural assembly having a cured bondline. The cured bondline comprises an adhesive layer, a scrim ply layer integrated with the adhesive layer, and an electrical sensor network integrated with the scrim ply layer. The system further comprises an electrical power source for providing electrical power to the electrical sensor network. The system further comprises a digital data communications network for retrieving and processing data from the electrical sensor network. The electrical sensor network monitors adhesive integrity within the cured bondline on demand by interpreting changes in local dynamic responses and electromechanical properties directly measured within the cured bondline.

In another embodiment of the disclosure, there is provided a system for monitoring adhesive integrity within a cured bondline of a bonded composite lamina assembly. The system comprises a bonded composite lamina assembly having a cured bondline. The cured bondline comprises an adhesive layer, a scrim ply layer integrated with the adhesive layer, and an electrical sensor network integrated with the scrim ply layer. The system further comprises a wireless electrical power source for providing electrical power to the electrical sensor network. The system further comprises a wireless digital data communications network for retrieving and processing data from the electrical sensor network. The electrical sensor network monitors adhesive integrity within the cured bondline on demand by interpreting changes in local dynamic responses and electromechanical properties directly measured within the cured bondline.

In another embodiment of the disclosure, there is provided a method for monitoring adhesive integrity within a cured bondline of a bonded structural assembly. The method comprises providing a bonded structural assembly having a cured bondline. The cured bondline comprises an adhesive layer, a scrim ply layer integrated with the adhesive layer, and an electrical sensor network integrated with the scrim ply layer. The method further comprises activating the electrical sensor network to monitor adhesive integrity of the cured bondline on demand by interpreting changes in local dynamic responses and electromechanical properties directly measured within the cured bondline. The method further comprises retrieving and processing adhesive integrity data of the cured bondline from the electrical sensor network via a digital data communications network.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary embodiments, but which are not necessarily drawn to scale, wherein.

DETAILED DESCRIPTION

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and complete and will fully convey the scope of the disclosure to those skilled in the art. The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

Figure 1:
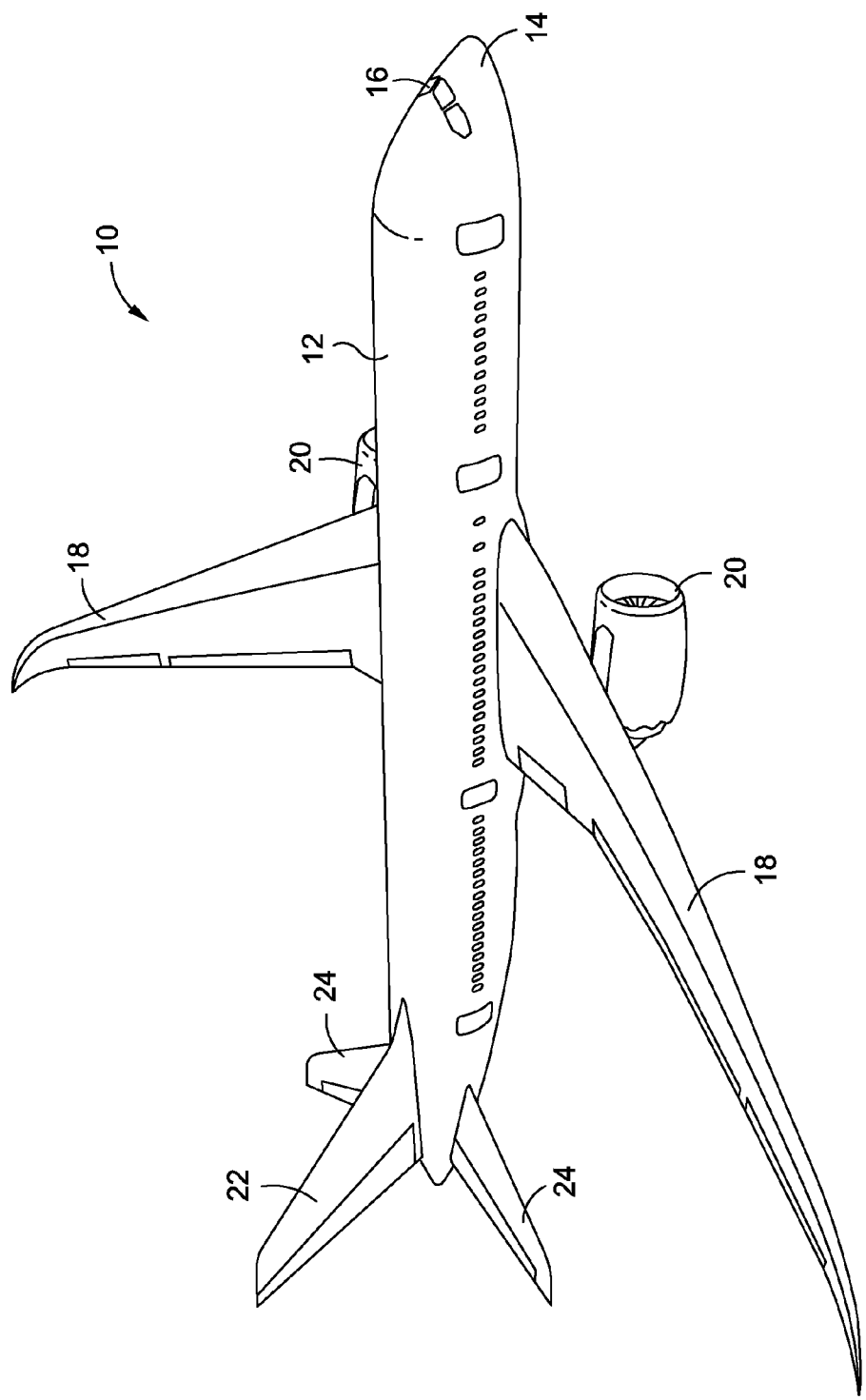
FIG. 1 is an illustration of a perspective view of an exemplary aircraft for which one of the embodiments of the system and method of the disclosure may be used.

Now referring to the Figures, FIG. 1 is an illustration of a perspective view of an exemplary prior art aircraft 10 for which one of the embodiments of a system 30 (see FIG. 2) or a system 100 (see FIG. 3), or a method 200 (see FIG. 9) for monitoring adhesive integrity may be used. The aircraft 10 comprises a fuselage 12, a nose 14, a cockpit 16, wings 18 operatively coupled to the fuselage 12, one or more propulsion units 20, a tail vertical stabilizer 22, and one or more tail horizontal stabilizers 24. Although the aircraft 10 shown in FIG. 1 is generally representative of a commercial passenger aircraft, the systems 30, 100 and method 200 disclosed herein may also be employed in other types of aircraft. More specifically, the teachings of the disclosed embodiments may be applied to other passenger aircraft, cargo aircraft, military aircraft, rotorcraft, and other types of aircraft or aerial vehicles, as well as aerospace vehicles such as satellites, space launch vehicles, rockets, and other types of aerospace vehicles. It may also be appreciated that embodiments of systems, methods and apparatuses in accordance with the disclosure may be utilized in other vehicles, such as boats and other watercraft, trains, automobiles, trucks, buses, and other types of vehicles.

Figure 2:
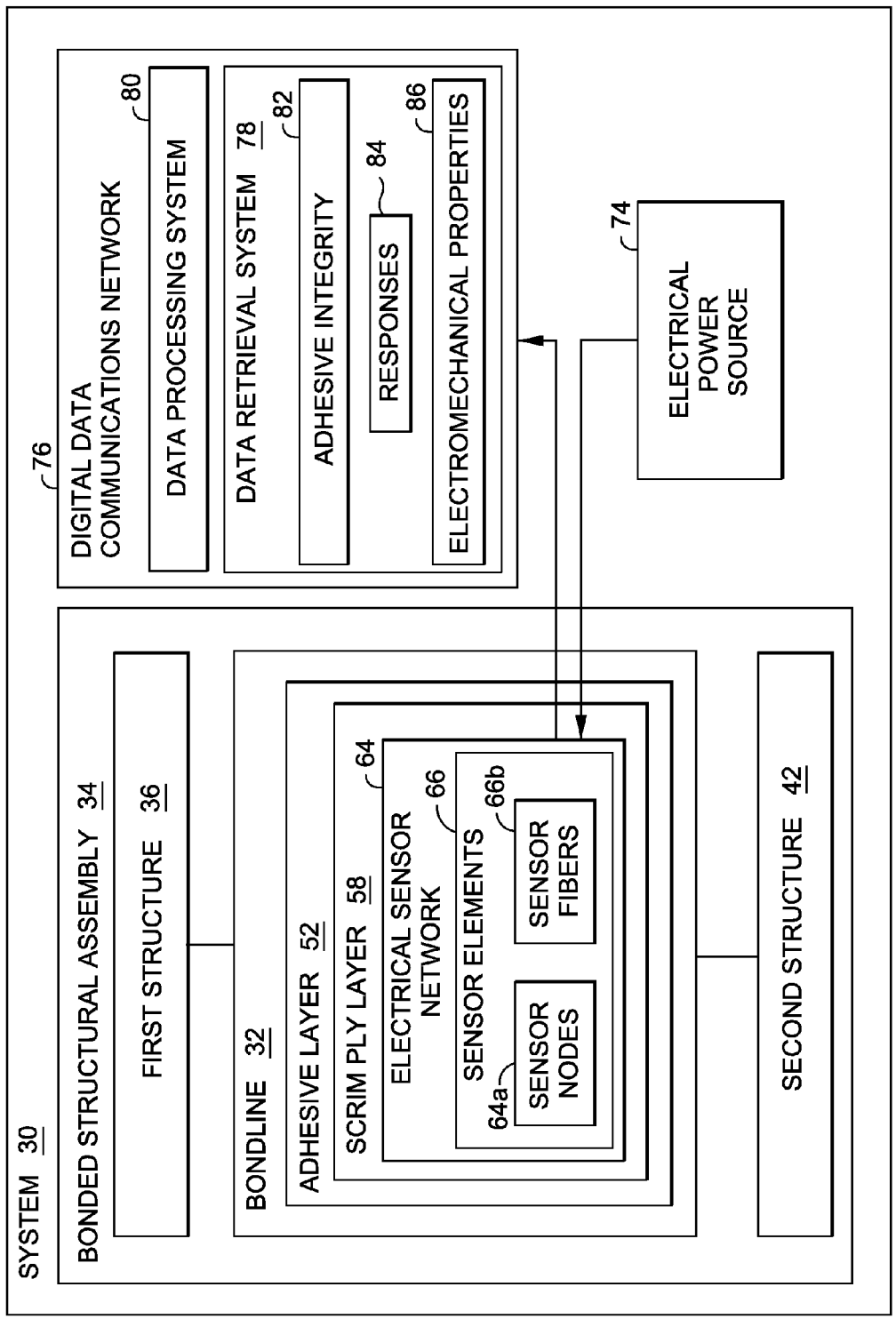
FIG. 2 is an illustration of a block diagram of one of the embodiments of a system for monitoring adhesive integrity of the disclosure.

FIG. 2 is an illustration of a block diagram of one of the embodiments of the system 30 for monitoring adhesive integrity. In one embodiment of the disclosure, there is provided the system 30 for monitoring adhesive integrity within a cured bondline 32 or joint of a bonded structural assembly 34. As used herein, the term "adhesive integrity" means a measure of the quality, soundness, effectiveness, performance, and strength of an adhesive bond and the ability of the adhesive bond to function reliably as required throughout the predicted lifetime of a bonded structural assembly or structure.

Figure 4A:
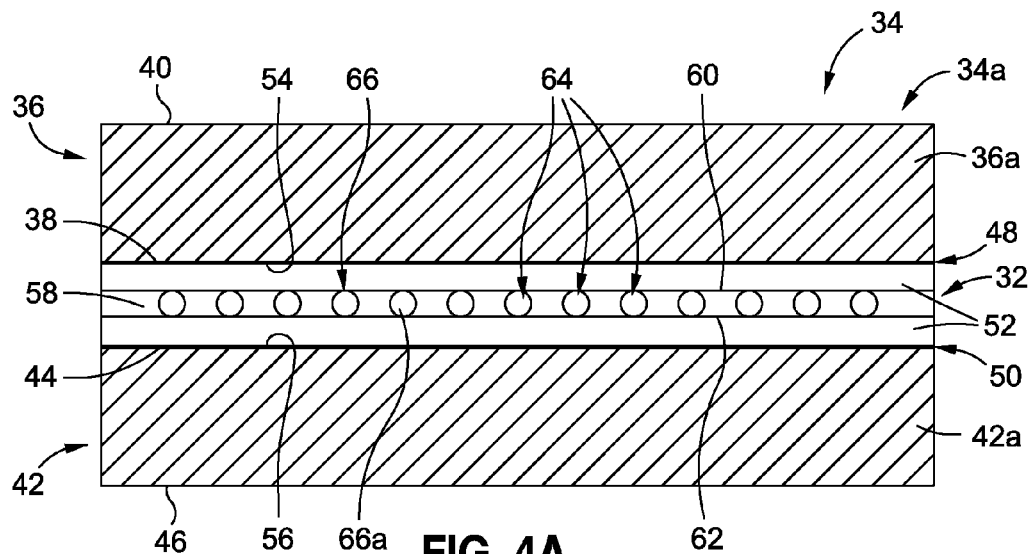
FIG. 4A is an illustration of a partial cross-sectional view of an embodiment of a bonded structure having one of the embodiments of the system of the disclosure.
Figure 4B:
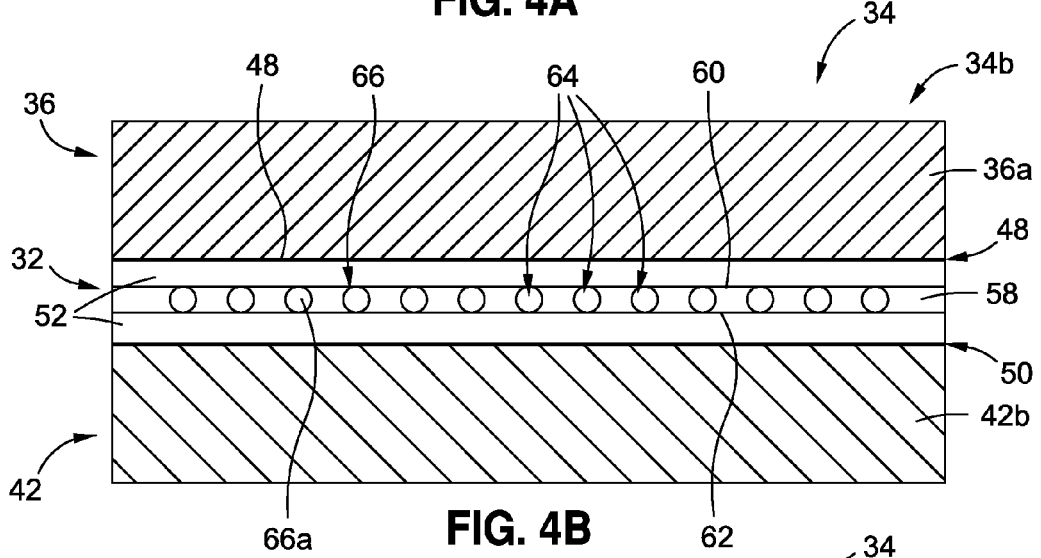
FIG. 4B is an illustration of a partial cross-sectional view of another embodiment of a bonded structure having one of the embodiments of the system of the disclosure.
Figure 4C:
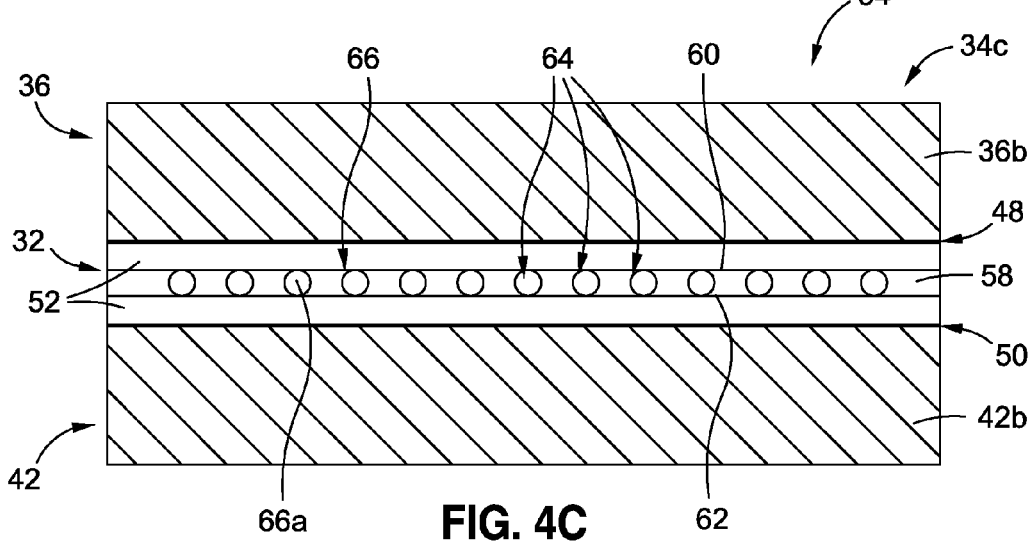
FIG. 4C is an illustration of a partial cross-sectional view of another embodiment of a bonded structure having one of the embodiments of the system of the disclosure.

The system 30 comprises the bonded structural assembly 34 having the cured bondline 32 or joint. As shown in FIGS. 4A-4C, the bonded structural assembly 34 may comprise a first structure 36 and a second structure 42. The first structure 36 has a first side 38 and a second side 40. The second structure 42 has a first side 44 and a second side 46. The first structure 36 may be made of a composite material, a metal material, a combination of a composite material and a metal material, or another suitable material. The second structure 36 may be made of a composite material, a metal material, a combination of a composite material and a metal material, or another suitable material. Preferably, the composite material for the first structure 36 and/or the second structure 42 comprises polymeric composites, fiber-reinforced composite materials, fiber-reinforced polymers, carbon fiber reinforced plastics (CFRP), glass-reinforced plastics (GRP), thermoplastic composites, thermoset composites, epoxy resin composites, shape memory polymer composites, ceramic matrix composites, or another suitable composite material. Exemplary composite material may typically comprise a reinforcement fiber, such as reinforcement fabric, dispersed in a thermoplastic or thermoset polymer matrix. Reinforcement fabrics may comprise fibers made of metallic, carbon, glass, boron, ceramic, and polymeric fibers. The reinforcement fibers may be in woven or non-woven mats, or they may be dispersed in the matrix. Matrix material may comprise thermoplastic materials such as polyamides, polyolefins and fluoropolymers, and thermosets such as epoxies and polyesters. Preferably, the metal material for the first structure 36 and/or the second structure 42 comprises aluminum, stainless steel, titanium, alloys thereof, or another suitable metal or metal alloy.

FIG. 4A is an illustration of a partial cross-sectional view of an embodiment of a bonded structure 34a having a first structure 36a made of one material, such as a metal, and having a second structure 42a made of the same material, such as a metal, as the material of the first structure 36a. FIG. 4B is an illustration of a partial cross-sectional view of another embodiment of a bonded structure 34b having the first structure 36a made of one material, such as a metal, and having a second structure 42b made of a different material, such as a composite, than the material of the first structure 36a. FIG. 4C is an illustration of a partial cross-sectional view of another embodiment of a bonded structure 34c having a first structure 36b made of one material, such as a composite, and having the second structure 42b made of the same material, such as a composite, as the material of the first structure 36b.

As shown in FIGS. 4A-4C, the cured bondline 32 or joint of the bonded structural assembly 34 comprises an adhesive layer or layers 52. As shown in FIG. 4A, the adhesive layer 52 has a first side 54 and a second side 56. The adhesive layer or layers 52 may comprise an adhesive material such as an epoxy adhesive, a polyurethane adhesive, a toughened acrylic adhesive, or another suitable adhesive. Epoxy adhesives generally have good strength, low shrinkage, and produce strong durable bonds with most materials. Polyurethane adhesives generally are fast curing, provide strong resilient joints which are impact resistant, and have good low temperature strength. Toughened acrylic adhesives generally are fast curing, have high strength and toughness, and bond well to a variety of materials.

As shown in FIG. 2, the cured bondline 32 further comprises a scrim ply layer 58 integrated with the adhesive layer or layers 52 (see also FIGS. 4A-4C and 5A-5B). As shown in FIG. 4A, the scrim ply layer 58 has a first side 60 and a second side 62. The scrim ply layer 58 preferably comprises a material fabricated from various fiber materials, such as nylon fiber material, polyester fiber material, glass fiber material, or another suitable fiber material. The scrim ply layer 58 is preferably multifunctional and acts as an adhesive layer by being integrated in the adhesive layers 52 and also acts as a bondline monitoring system.

As shown in FIGS. 4A-4C, the cured bondline 32 further comprises an electrical sensor network 64 integrated with the scrim ply layer 58. The electrical sensor network 64 preferably comprises a plurality of spaced sensor elements 66. The sensor elements 66 may comprise active sensor nodes 66a (see FIG. 6), active sensor fibers 66b (see FIG. 7), active sensor wires (not shown), sensor fiber optic wires (not shown), sensor coatings on fibers (not shown), carbon nanotubes (not shown), passive sensors, or another suitable sensor element. The sensor elements 66 may be comprised of a matrix of high-resistivity, insulative thermoplastic or thermoset polymer and conductive fillers, such as carbon black, carbon nanotubes, and metallic particles, such as silver, nickel and aluminum, although other conductive and semiconductive particles such as metallic oxides may be used. The sensor elements 66 may also comprise electrode sensors, piezoelectric sensors, pulse-echo (PE) sensors, pitch-catch active sensors, through transmission (TT) sensors, shear wave sensors, resonance sensors, mechanical impedance sensors, lamb wave sensors, rayleigh wave sensors, stoneley wave sensors, or other suitable sensors. Preferably, the sensor elements 66 are active sensors. However, passive sensors may also be used. Active sensors may generate electric current or voltage directly in response to environmental stimulation. Passive sensors may produce a change in some passive electrical quantity, such as capacitance, resistance, or inductance, as a result of stimulation and typically may require additional electrical energy for excitation. Some RFID devices may be active and some RFID devices may be passive.

The sensor elements 66 may be removable and placed manually on the scrim ply layer 58 integrated with the adhesive layer 52 and later removed. Alternatively, the sensor elements 66 may be bonded or otherwise attached to or within the scrim ply layer 58 by an adhesive or one or more mechanical fasteners (not shown). The sensor elements 66 may be small discrete sensors in the form of strips or electrodes covering some or substantially all of the surface portions of the scrim ply layer 58 or in the form of mats, fibers or woven sheets attached to or on the scrim ply layer 58.

The system 30 integrates the sensing of the cured bondline 32 into the bonded structural assembly 34 and provides a method to interrogate the characteristics and integrity of the cured bondline 32 on demand or continuously. The smart adhesive layer 52 and the scrim ply layer 58 may be a permanent part of the bonded structural assembly 34. The monitoring system 30 provides for an internal electrical sensor network 64 and internal sensor elements 66 at or within the cured bondline 32 to provide for direct measurement and assessment of the bondline characteristics and bondline integrity directly at or within the cured bondline 32 itself.

Figure 6:
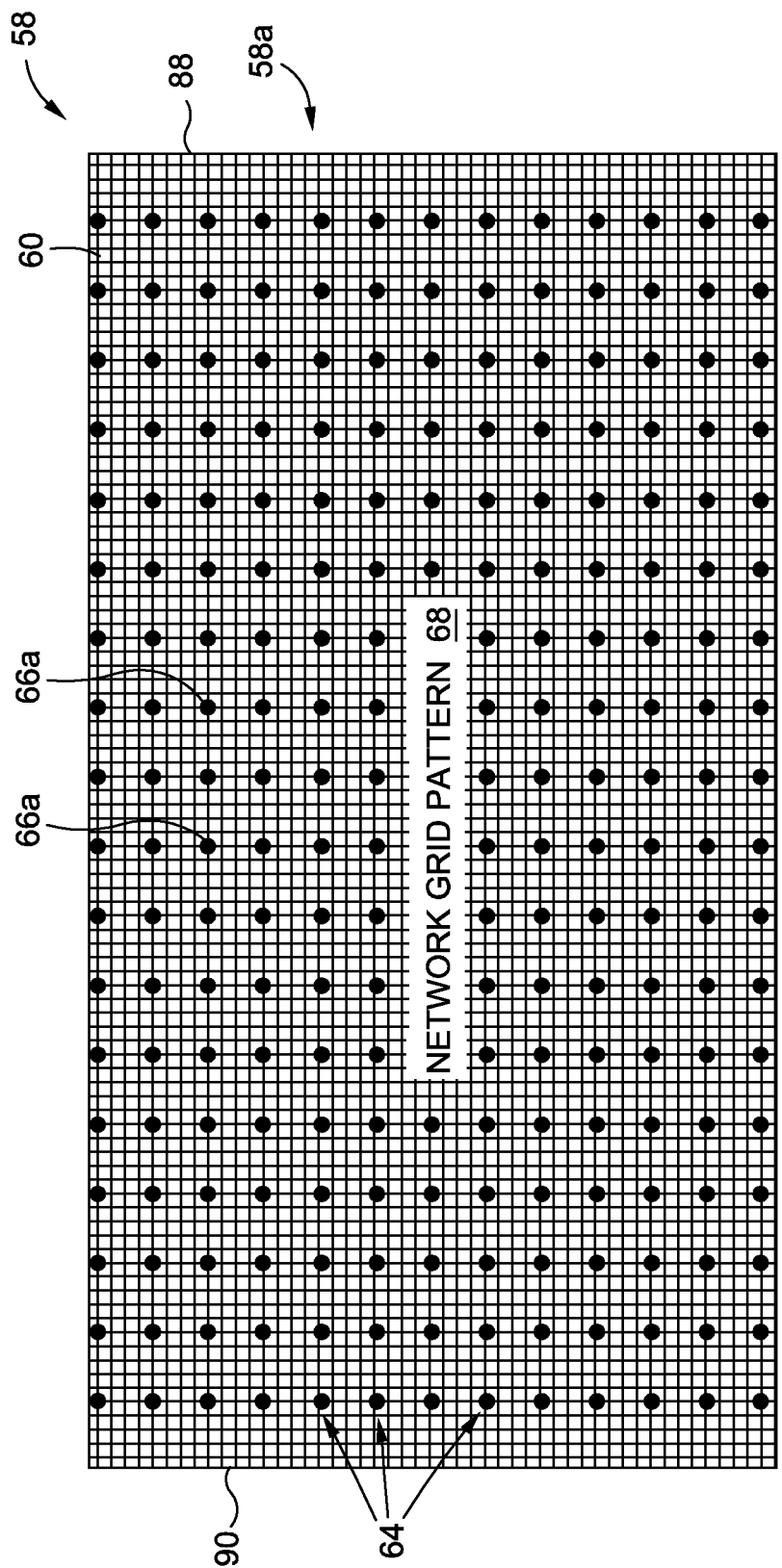
FIG. 6 is an illustration of a top view of one of the embodiments of a scrim ply layer with active sensor nodes.

The sensor elements 66 preferably have modalities based on ultrasonic wave propagation and electromechanical impedance. In order to enable the smart scrim ply layer 58, the sensor elements 66 may be integrated into the woven or random mat fiber layer of the scrim material. In one embodiment, scrim material with the sensor elements 66 may be laminated into the adhesive layer 52 to provide an integrated film adhesive scrim ply layer 58 (see FIG. 6) with sensing capabilities. FIG. 6 is an illustration of a top view of one of the embodiments of the scrim ply layer 58 in the form of a scrim ply layer 58a with an electrical sensor network 64 having sensor elements 66 in the form of active sensor nodes 66a integrated into or attached onto the scrim ply layer 58. As shown in FIG. 6, the sensor nodes 66a form a network grid pattern 68. As shown in FIGS. 4A and 6, the scrim ply layer 58 has a first side 60 (see FIGS. 4A and 6), a second side 62 (see FIG. 4A), a first end 88 (see FIG. 6) and a second end 90 (see FIG. 6).

Figure 5A:
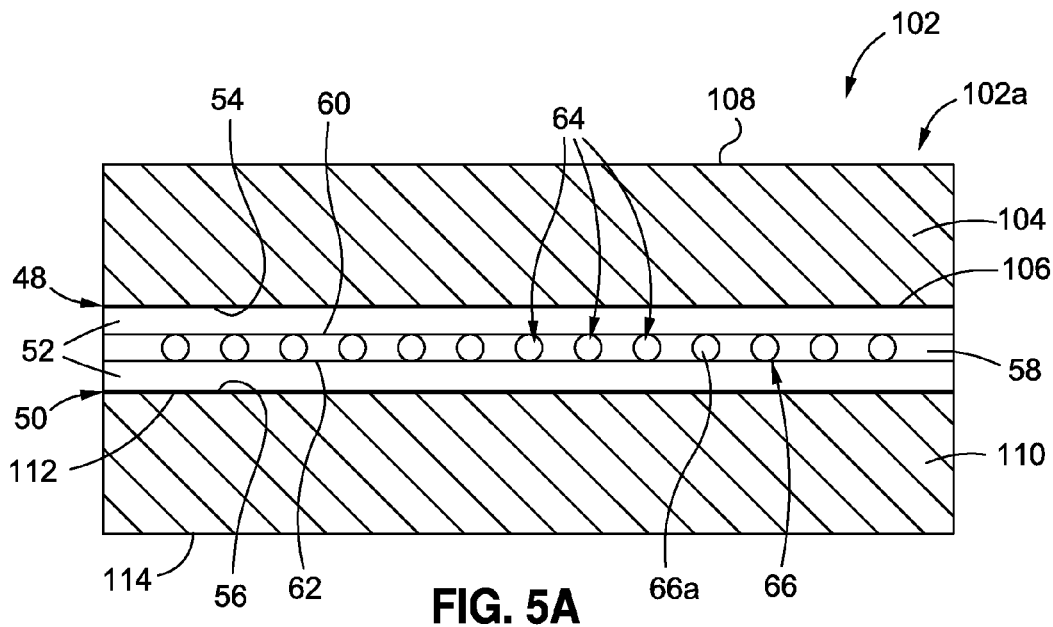
FIG. 5A is an illustration of a partial cross-sectional view of an embodiment of a bonded structure having one of the embodiments of the electrical sensor network of the disclosure.
Figure 5B:
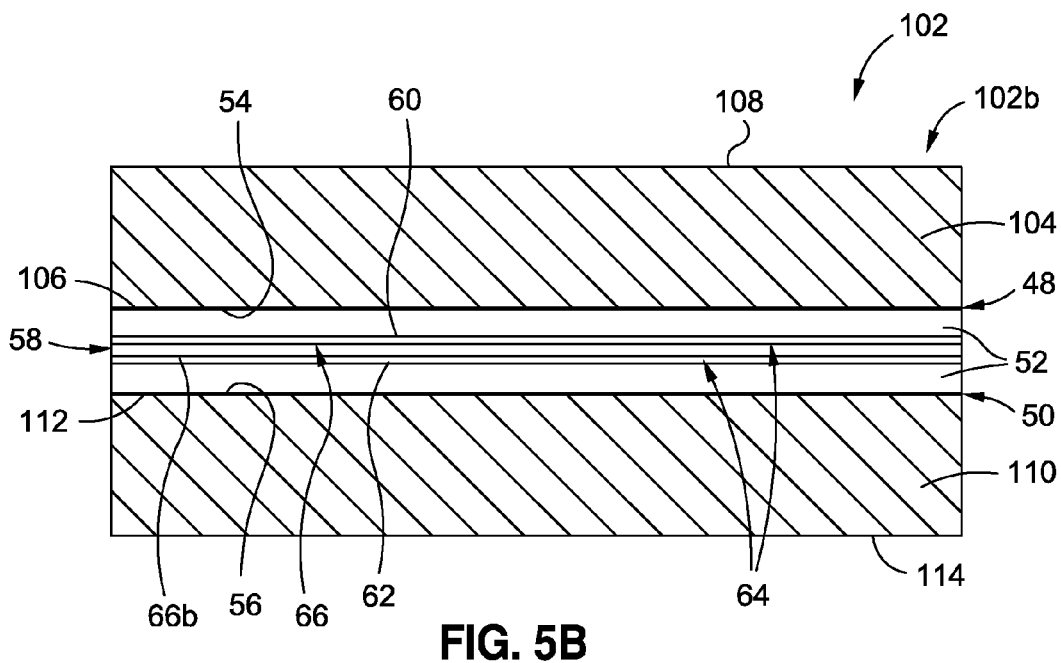
FIG. 5B is an illustration of a partial cross-sectional view of another embodiment of a bonded structure having another one of the embodiments of the electrical sensor network of the disclosure.
Figure 7:
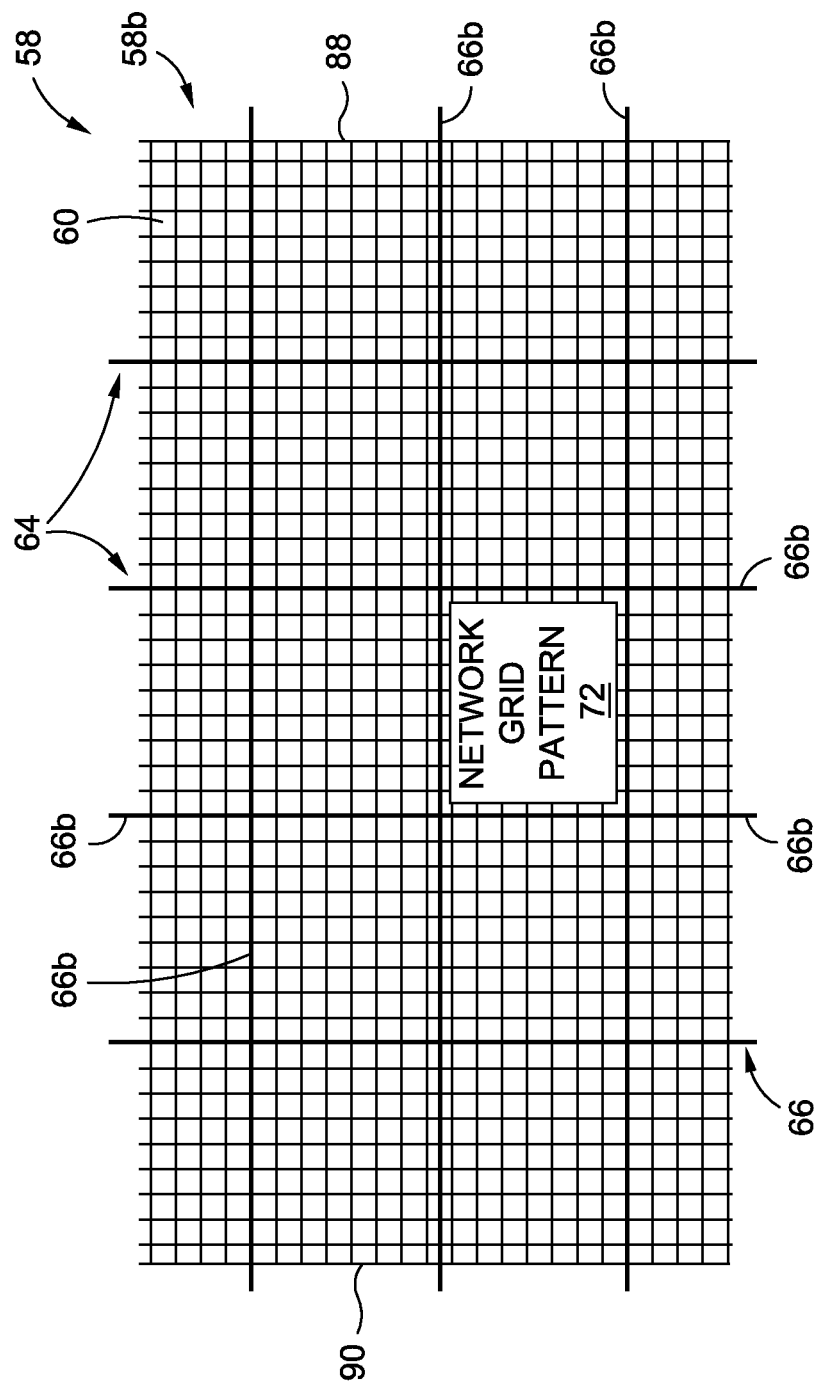
FIG. 7 is an illustration of a top view of another one of the embodiments of a scrim ply layer with sensor fibers.

In another embodiment, sensor elements 66 may be attached or integrated into an existing or known scrim ply layer 58 (see FIG. 7) integrated with the adhesive layer 52. FIG. 7 is an illustration of a top view of another one of the embodiments of the scrim ply layer 58 in the form of a scrim ply layer 58b with an electrical sensor network 64 having sensor elements 66 in the form of active sensor fibers 66b integrated into or attached onto the scrim ply layer 58. As shown in FIG. 7, the sensor fibers 66b form a network grid pattern 72. As shown in FIGS. 5B and 7, the scrim ply layer 58 has a first side 60 (see FIGS. 5B and 7), a second side 62 (see FIG. 5B), a first end 88 (see FIG. 7) and a second end 90 (see FIG. 7).

As shown in FIG. 2, the system 30 further comprises an electrical power source 74 for providing electrical power to the electrical sensor network 64. The electrical power source 74 may comprise batteries, voltage, RFID (radio frequency identification), magnetic induction transmission, or another suitable electrical power source. The electrical power source 74 is preferably wireless.

As shown in FIG. 2, the system 30 further comprises a digital data communications network 76 for retrieving and processing data from the electrical sensor network 64. The digital data communications network 76 is preferably wireless. The digital data communications network 76 may comprise a data retrieval system 78 for retrieving data from the electrical sensor network 64. The data retrieval system 78 may comprise RFID, a radio transceiver (a device that has both a transmitter and a receiver which are combined and share common circuitry or a single housing), or another suitable data retrieval system.

The electrical sensor network 64 monitors adhesive integrity 82 (see FIG. 2) within the cured bondline 32 on demand by interpreting changes in local dynamic responses 84 (see FIG. 2) and electromechanical properties 86 (see FIG. 2) directly measured at or within the cured bondline 32. The electrical sensor network 64 may also continuously monitor the adhesive integrity 82 within the cured bondline 32. The local dynamic responses 84 and the electromechanical properties 86 are preferably directly measured at or within the cured bondline and may comprise disbonds 92 (see FIG. 8), weak bonding 94 (see FIG. 8), strain levels, moisture ingression, materials change, cracks, voids, delamination, porosity, or other suitable local dynamic responses or electromechanical properties or other irregularities which may adversely affect the performance of the cured bondline 32 of the bonded structural assembly 34. The integrity of the cured bondline 32 may be determined by interpreting changes in local dynamic responses 84 and electromechanical properties 86 directly measured at or within the cured bondline 32. Additional sensor elements 66, such as fiber optic based materials to assess moisture ingression, piezoelectric sensors to assess strain, or other sensing methods may also be incorporated into the adhesive layer 52. Other functional aspects of the scrim ply layer 58 may also be maintained, including control of bondline thickness, bondline tack control, and/or adhesive uniformity of the bondline.

As shown in FIG. 2, the digital data communications network 76 may further comprise a data processing system 80 for processing data from the electrical sensor network 64. The data processing system 80 may comprise, for example, a known computer processor (not shown), a database (not shown), and a data storage and management system (not shown).

The system 30 monitors adhesive integrity 82 within the cured bondline 32 of the bonded structural assembly 34. Preferably, the system 30 is used for monitoring adhesive integrity at or within the cured bondline 32 of bonded structural assemblies 34, such as bonded structural assemblies for use in aircraft 10 (see FIG. 1), spacecraft, aerospace vehicles, space launch vehicles, rockets, satellites, rotorcraft, watercraft, boats, trains, automobiles, trucks, buses, architectural structures, or other suitable vehicles and structures.

Figure 3:
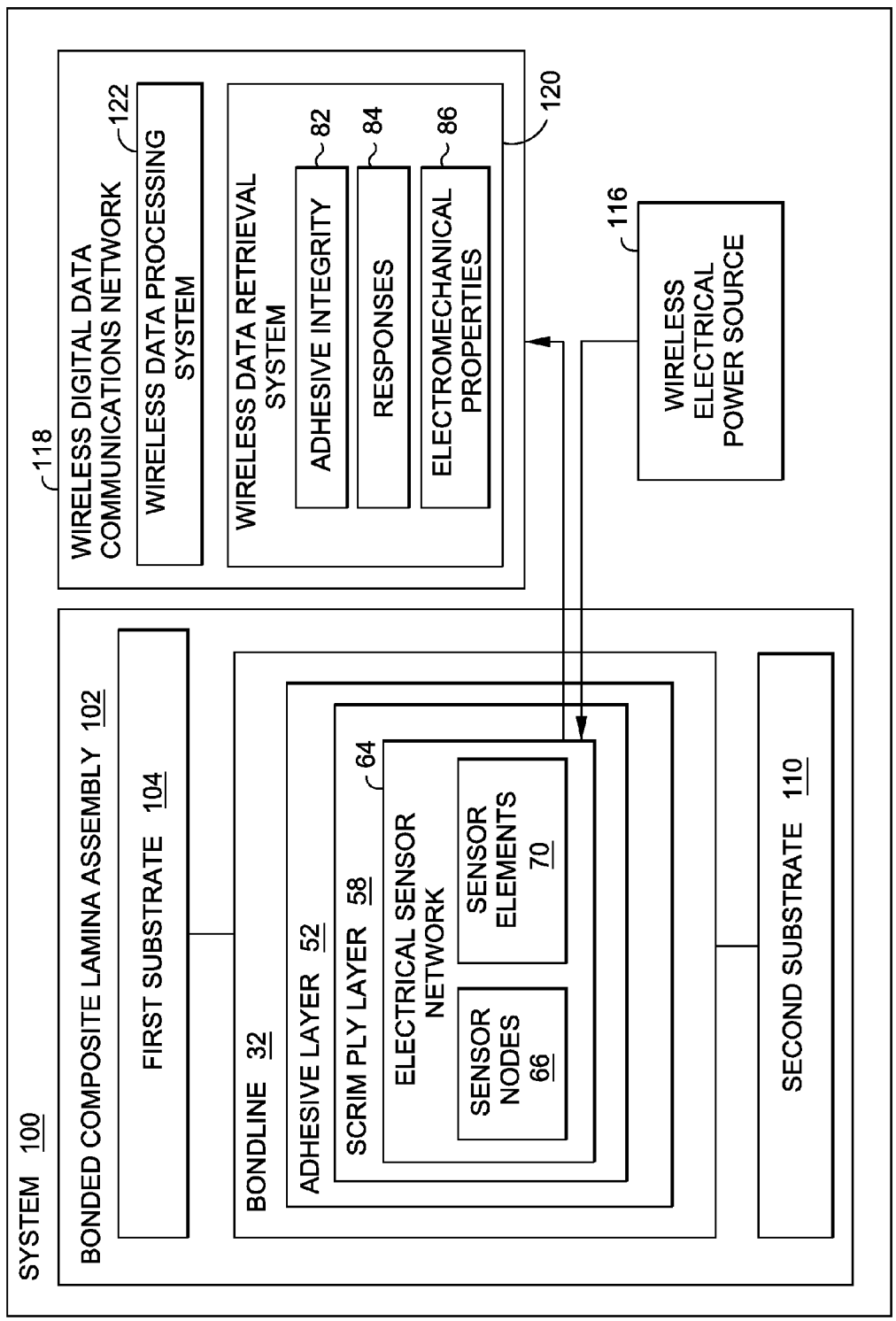
FIG. 3 is an illustration of a block diagram of another one of the embodiments of a system for monitoring adhesive integrity of the disclosure.

FIG. 3 is an illustration of a block diagram of another one of the embodiments of a system 100 for monitoring adhesive integrity within the cured bondline 32 of a bonded composite lamina assembly 102. The system 100 comprises the bonded composite lamina assembly 102 have the cured bondline 32. As shown in FIGS. 5A-5B, the bonded composite lamina assembly 102 may comprise a first substrate 104 and a second substrate 110. The first substrate 104 has a first side 106 and a second side 108. The second substrate 110 has a first side 112 and a second side 114. The first substrate 104 and the second substrate 110 are preferably both made of a composite material comprising polymeric composites, fiber-reinforced composite materials, fiber-reinforced polymers, carbon fiber reinforced plastics (CFRP), glass-reinforced plastics (GRP), thermoplastic composites, thermoset composites, epoxy resin composites, shape memory polymer composites, ceramic matrix composites, or another suitable composite material. FIG. 5A is an illustration of a partial cross-sectional view of an embodiment of a bonded structure 102a having one of the embodiments of the electrical sensor network 64 of the disclosure. As shown in FIG. 5A, the electrical sensor network 64 comprises sensor elements 66 comprising active sensor nodes 66a. FIG. 5B is an illustration of a partial cross-sectional view of another embodiment of a bonded structure 102b having another one of the embodiments of the electrical sensor network 64 of the disclosure. As shown in FIG. 5B, the electrical sensor network 64 comprises sensor elements 66 comprising active sensor fibers 66b.

As shown in FIGS. 5A-5B, the cured bondline 32 of the bonded structural assembly 102 comprises adhesive layer or layers 52. The adhesive layer or layers 52 may comprise an adhesive material such as an epoxy adhesive, a polyurethane adhesive, a toughened acrylic adhesive, or another suitable adhesive. The cured bondline 32 further comprises a scrim ply layer 58 integrated with the adhesive layer or layers 52. As shown in FIG. 5A, the scrim ply layer 58 has a first side 60 and a second side 62. The scrim ply layer 58 preferably comprises a material fabricated from various fiber materials, such as nylon fiber material, polyester fiber material, glass fiber material, or another suitable fiber material. The scrim ply layer 58 is multifunctional and acts as an adhesive layer by being integrated in the adhesive layer 52 and also acts as a bondline monitoring system. The cured bondline 32 further comprises an electrical sensor network 64 integrated with the scrim ply layer 58. The electrical sensor network 64 preferably comprises a plurality of spaced sensor elements 66 comprising active sensor nodes 66a (see FIG. 5A), active sensor fibers 66b (see FIG. 5B), active sensor wires (not shown), sensor fiber optic wires (not shown), sensor coatings on fibers (not shown), carbon nanotubes (not shown), passive sensors, or another suitable sensor element. The sensor elements 66 preferably have modalities based on ultrasonic wave propagation and electromechanical impedance. The monitoring system 100 provides for an internal electrical sensor network 64 and internal sensor elements 66 at or within the cured bondline 32 to provide for direct measurement and assessment of the bondline characteristics and bondline integrity directly at or within the cured bondline 32 itself.

As shown in FIG. 3, the system 100 further comprises a wireless electrical power source 116 for providing electrical power to the electrical sensor network 64. The wireless electrical power source 74 may comprise batteries, voltage, RFID (radio frequency identification), magnetic induction transmission, or another suitable wireless electrical power source.

As shown in FIG. 3, the system 100 further comprises a wireless digital data communications network 118 for retrieving and processing data from the electrical sensor network 64. The wireless digital data communications network 118 may comprise a wireless data retrieval system 120 for retrieving data from the electrical sensor network 64. The wireless data retrieval system 120 may comprise RFID, a radio transceiver, or another suitable data retrieval system. The electrical sensor network 64 monitors adhesive integrity 82 (see FIG. 3) within the cured bondline 32 on demand by interpreting changes in local dynamic responses 84 (see FIG. 3) and electromechanical properties 86 (see FIG. 3) directly measured within the cured bondline 32. The electrical sensor network 64 may also continuously monitor the adhesive integrity 82 within the cured bondline 32. The local dynamic responses 84 and the electromechanical properties 86 are preferably directly measured at or within the cured bondline 32 and may comprise disbonds 92 (see FIG. 8), weak bonding 94 (see FIG. 8), strain levels, moisture ingression, materials change, cracks, voids, delamination, porosity, or other suitable local dynamic responses or electromechanical properties or other irregularities which may adversely affect the performance of the cured bondline 32 of the bonded composite lamina assembly 102. The integrity of the cured bondline 32 may be determined by interpreting changes in local dynamic responses 84 and electromechanical properties 86 directly measured at or within the cured bondline 32. Additional sensor elements 66, such as fiber optic based materials to assess moisture ingression, piezoelectric sensors to assess strain, or other sensing methods may also be incorporated into the adhesive layer 52. Other functional aspects of the scrim ply layer 58 may also be maintained, including control of bondline thickness, bondline tack control, and/or adhesive uniformity of the bondline.

As shown in FIG. 3, the wireless digital data communications network 118 may further comprise a wireless data processing system 122 for processing data from the electrical sensor network 64. The wireless data processing system 122 may comprise, for example, a known a computer processor (not shown), a database (not shown), and a data storage and management system (not shown).

The system 100 monitors adhesive integrity within the cured bondline 32 of the bonded composite lamina assembly 102. Preferably, the system 100 is used for monitoring adhesive integrity within the cured bondline 32 of bonded composite lamina assemblies 102, such as bonded composite lamina assemblies used in aircraft, spacecraft, aerospace vehicles, space launch vehicles, rockets, satellites, rotorcraft, watercraft, boats, trains, automobiles, trucks, buses, architectural structures, or other suitable vehicles and structures.

Figure 8:
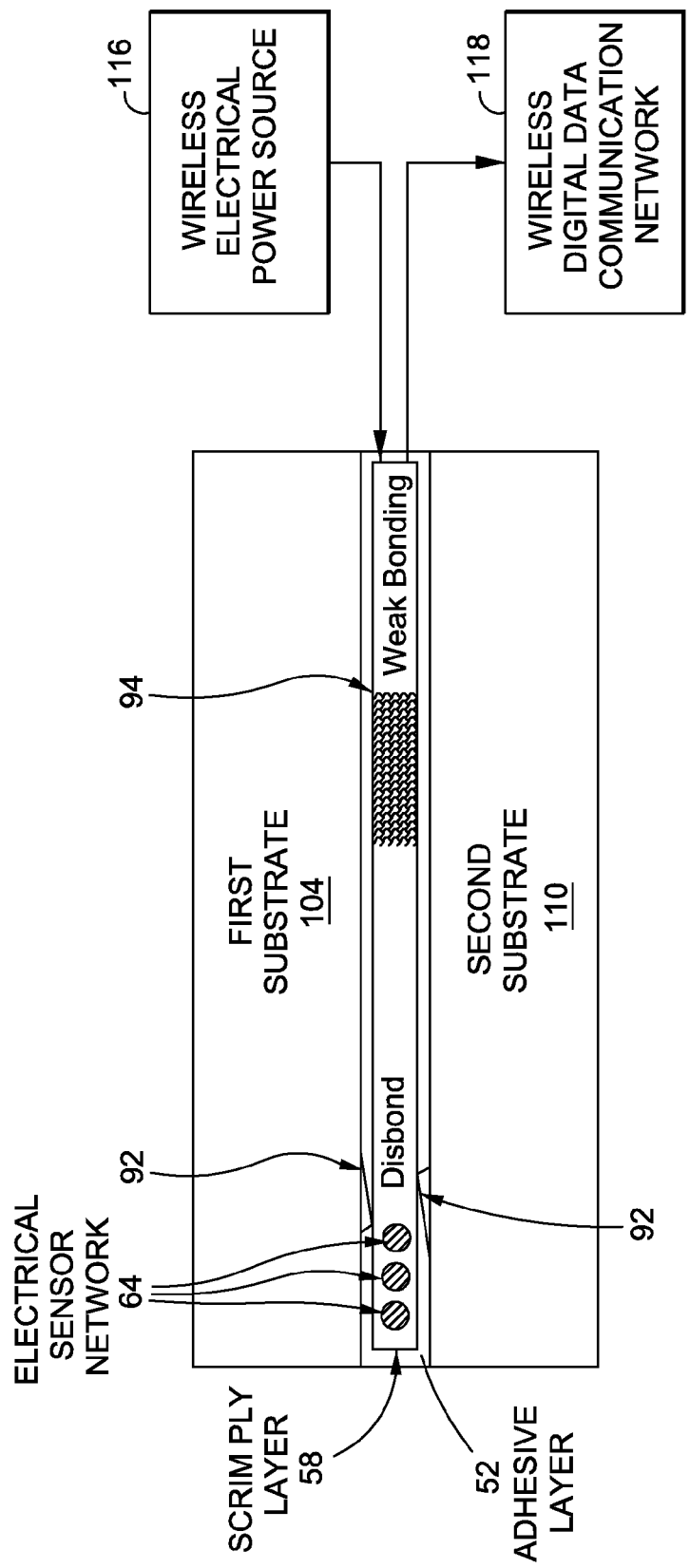
FIG. 8 is an illustration of a schematic diagram of one of the embodiments of a system of the disclosure showing detection of disbonds and weak bonding; and, FIG. 9 is an illustration of a flow diagram of an embodiment of a method for monitoring adhesive integrity of the disclosure.

FIG. 8 is an illustration of a schematic diagram of one of the embodiments of the system 100 of the disclosure showing detection of disbonds 92 and weak bonding 94. FIG. 8 shows the first substrate 104 bonded to the second substrate 110 with the scrim ply layer 58 integrated with the adhesive layer 52, and the scrim ply layer 58 having the electrical sensor network 64 integrated with the scrim ply layer 58. The wireless electrical power source 116 provides electrical power to the electrical sensor network 64 of the system 100. The adhesive layer 52 with the scrim ply layer 58 is shown with disbonds 92 and weak bonding 94. The wireless digital data communication network 118 processes the disbond 92 and weak bonding 94 data from the electrical sensor network 64 to monitor the health of the system 100.

Figure 9:
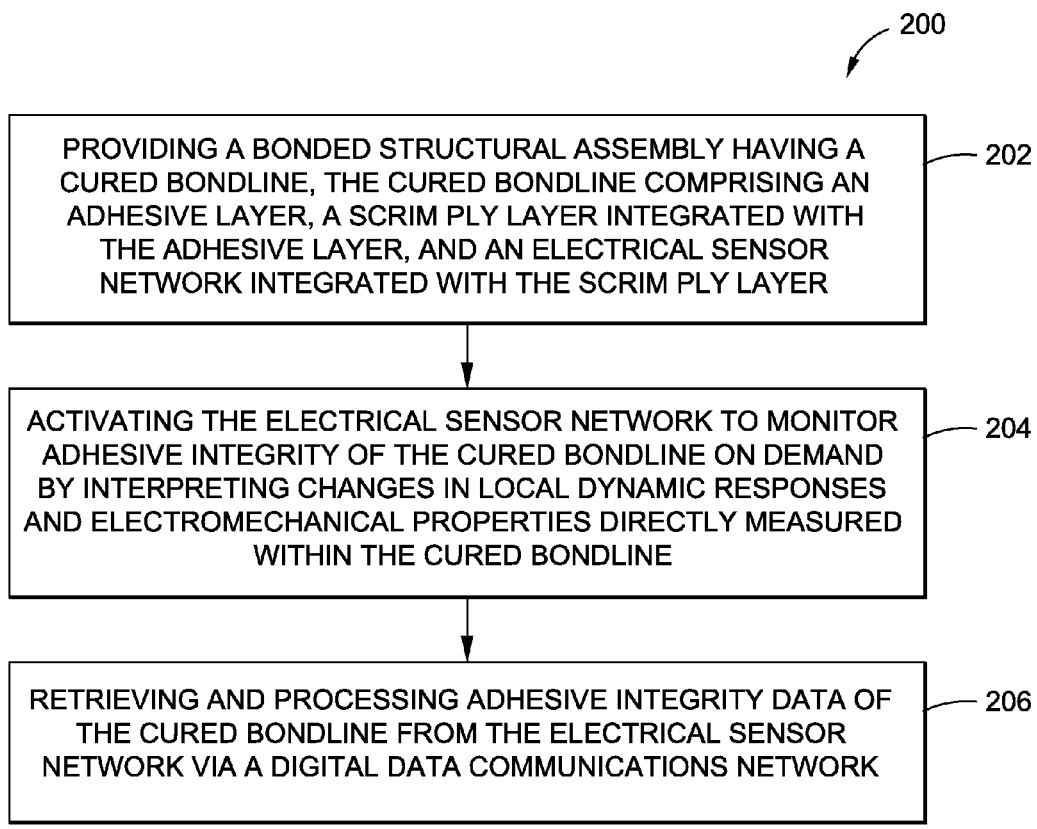

In another embodiment of the disclosure, there is provided a method 200 for monitoring adhesive integrity within a cured bondline 32 (see FIGS. 2, 3) of a bonded structural assembly 34 (see FIG. 2). FIG. 9 is an illustration of a flow diagram of an embodiment of a method 200 for monitoring adhesive integrity within the cured bondline 32. The method 200 comprises step 202 of providing the bonded structural assembly 34 (see FIGS. 4A-4C) having the cured bondline 32. The bonded structural assembly 34 may preferably comprise a bonded composite lamina assembly 102 (see FIG. 3). As discussed above and as shown in FIGS. 4A-4C, the bonded structural assembly 34 may comprise first structure 36 and second structure 42. The first structure 36 may be made of a composite material, a metal material, a combination thereof, or another suitable material. The second structure 36 may be made of a composite material, a metal material, a combination thereof, or another suitable material. Preferably, the composite material for the first structure 36 and/or the second structure 42 comprises polymeric composites, fiber-reinforced composite materials, fiber-reinforced polymers, carbon fiber reinforced plastics (CFRP), glass-reinforced plastics (GRP), thermoplastic composites, thermoset composites, epoxy resin composites, shape memory polymer composites, ceramic matrix composites, or another suitable composite material. Preferably, the metal material for the first structure 36 and/or the second structure 42 comprises aluminum, stainless steel, titanium, alloys thereof, or another suitable metal or metal alloy.

As discussed above, the cured bondline 32 comprises the adhesive layer 52, the scrim ply layer 58 integrated with the adhesive layer 52, and the electrical sensor network 64 integrated with the scrim ply layer 58. As shown in FIG. 4A, the adhesive layer 52 may comprise a first side 54 and a second side 56. As discussed above, the adhesive layer 52 may comprise an adhesive material such as an epoxy adhesive, a polyurethane adhesive, a toughened acrylic adhesive, or another suitable adhesive. As discussed above, the scrim ply layer 58 integrated with the adhesive layer 52 has a first side 60 and a second side 62. The scrim ply layer 58 preferably comprises a material fabricated from various fiber materials, such as nylon fiber material, polyester fiber material, glass fiber material, or another suitable fiber material. The scrim ply layer 58 may be multifunctional and act as an adhesive layer by being integrated in the adhesive layer 52 and may also act as a bondline monitoring system. As discussed above, the electrical sensor network 64 may comprise a plurality of spaced sensor elements 66 comprising active sensor nodes 66a, active sensor fibers 66b, active sensor wires (not shown), sensor fiber optic wires (not shown), sensor coatings on fibers (not shown), carbon nanotubes (not shown), passive sensors, or another suitable sensor element. The sensor elements 66 preferably have modalities based on ultrasonic wave propagation and electromechanical impedance. The method 200 provides for an internal electrical sensor network 64 and internal sensor elements 66 at or within the cured bondline 32 to provide for direct measurement and assessment of the bondline characteristics and bondline integrity directly at or within the cured bondline 32 itself.

As shown in FIG. 9, the method 200 further comprises step 204 of activating the electrical sensor network 64 (see FIGS. 4A-4C) to monitor adhesive integrity 82 of the cured bondline 32 on demand by interpreting changes in local dynamic responses 84 and electromechanical properties 86 (see FIG. 2) directly measured within the cured bondline 32. Preferably, the electrical sensor network 64 is activated with an electrical power source 74 (see FIG. 2), and more preferably, with a wireless electrical power source 116 (see FIG. 3). The electrical power source 74 or wireless electrical power source 116 may comprise batteries, voltage, RFID (radio frequency identification), magnetic induction transmission, or another suitable wireless electrical power source.

As shown in FIG. 9, the method 200 further comprises step 206 of retrieving and processing adhesive integrity data of the cured bondline 32 from the electrical sensor network 64 via the digital data communications network 76 (see FIG. 2). Preferably, the digital data communications network is a wireless digital data communications network 118 (see FIG. 3). The digital data communications network 76 may comprise a data retrieval system 78 for retrieving data from the electrical sensor network 64. The data retrieval system 78 may comprise RFID, a radio transceiver, or another suitable data retrieval system. The wireless digital data communications network 118 may comprise a wireless data retrieval system 120 for retrieving data from the electrical sensor network 64. The electrical sensor network 64 monitors adhesive integrity 82 (see FIGS. 2, 3) within the cured bondline 32 on demand by interpreting changes in local dynamic responses 84 (see FIGS. 2, 3) and electromechanical properties 86 (see FIGS. 2, 3) directly measured within the cured bondline 32. The electrical sensor network 64 may also continuously monitor the adhesive integrity 82 within the cured bondline 32. The local dynamic responses 84 and the electromechanical properties 86 are preferably directly measured at or within the cured bondline 32 and may comprise disbonds 92 (see FIG. 8), weak bonding 94 (see FIG. 8), strain levels, moisture ingression, materials change, cracks, voids, delamination, porosity, or other suitable local dynamic responses or electromechanical properties or other irregularities which may adversely affect the performance of the cured bondline of the bonded structural assembly. The integrity of the cured bondline 32 may be determined by interpreting changes in local dynamic responses 84 and electromechanical properties 86 directly measured at or within the cured bondline 32.

The digital data communications network 76 may further comprise a data processing system 80 for processing data from the electrical sensor network 64. The wireless digital data communications network 118 may further comprise a wireless data processing system 122 for processing data from the electrical sensor network 64. The data processing system 80 and the wireless data processing system 122 may comprise, for example, a known computer processor (not shown), a database (not shown), and a data storage and management system (not shown).

The method 200 monitors adhesive integrity within the cured bondline 32 of the bonded structural assembly 34, and preferably, monitors adhesive integrity within the cured bondline 32 of the bonded composite lamina assembly 102. Preferably, the method 200 is used for monitoring adhesive integrity within the cured bondline 32 of bonded structural assemblies 34, preferably bonded composite lamina assemblies 102, such as used in aircraft, spacecraft, aerospace vehicles, space launch vehicles, satellites, rotorcraft, watercraft, boats, trains, automobiles, trucks, buses, architectural structures, or other suitable vehicles and structures.

Embodiments of the monitoring systems 30, 100 and monitoring method 200 provide for the integration of active sensing materials into an adhesive scrim ply layer 58 to create a multifunctional system or matrix capable of serving as both an adhesive layer and a bondline monitoring system. The sensor elements 66 integrated into the adhesive scrim ply layer 58 matrix interpret changes within the local dynamic responses 84 and the electromechanical properties 86 measured within the bondline interface, and the sensor elements 66 may assess key characteristics such as disbonds, strain levels, moisture ingression, materials changes, cracks, voids, delamination, porosity, and/or other key characteristics at or within the cured bondline interface. Embodiments of the monitoring systems 30, 100 and monitoring method 200 may utilize various sets of active sensor elements 66, such as sensing materials with modalities based on ultrasonic wave propagation and electromechanical impedance based on the scrim meshing pattern, to perform as a power and information network. Activation of the system and data retrieval may be performed wirelessly using a wireless electrical power source 116, a wireless data retrieval system 120, and a wireless data processing system 122 for interpretation of data in situ at the cured bondline 32 of the structural assembly such as the bonded composite lamina assembly 102. Embodiments of the monitoring systems 30, 100 and monitoring method 200 provide a cured bondline 32 with an embedded multifunctional scrim ply layer 58 to monitor on demand or continuously for a change in the bondline interface adhesive integrity quality during both manufacturing and in-service. Such cured bondlines or bonded joints may reduce the overall weight of the structures and structural components by reducing the volume of heavy joints based on the use of fasteners. Bonded joints accomplish this, in part, by spreading the load over a larger footprint.

Embodiments of the monitoring systems 30, 100 and monitoring method 200 may provide monitoring of adhesive integrity at or within the cured bondline 32 in bonded structural assemblies used in aircraft, spacecraft, aerospace vehicles, space launch vehicles, rockets, satellites, rotorcraft, watercraft, boats, trains, automobiles, trucks, buses, and other suitable transport vehicles and structures. Embodiments of the monitoring systems 30, 100 and monitoring method 200 may provide in situ non-destructive systems and method for characterizing bonding properties and ensuring the bondline integrity of structurally bonded parts continuously throughout the service lifetime of the hardware and structurally bonded parts.

Embodiments of the monitoring systems 30, 100 and monitoring method 200 have the ability to interrogate the cured bondline while the structure or structural component parts are in-service; may decrease costs and flow time to the process of assuring bondline integrity; may be carried out on demand on a real time basis or continuously on a real time basis so that the information about the bondline integrity is available at all times; and, may predict and monitor the integrity, health and fitness of cured bondlines or bonded joints located remotely, interior, or beneath the structural surface without having to disassemble or remove structures or structural components or drill holes into the structures or structural components for insertion of any measurement tools. Moreover, embodiments of the monitoring systems 30, 100 and monitoring method 200 may provide for an internal electrical sensor network and internal sensors at or within the cured bondline to provide for direct measurement and assessment of the bondline characteristics and bondline integrity directly at or within the bondline itself. Finally, embodiments of the monitoring systems 30, 100 and monitoring method 200 may be used to predict deterioration or weaknesses directly at or within the cured bondline or bonded joint prior to the actual development of such deterioration or weaknesses, and thus, may increase reliability of the structure or structural component parts, may increase the safety of the adhesive bondline, and may reduce overall manufacturing and maintenance costs over the life of the structure or structural component parts.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation.

What is claimed is:

1. A system for monitoring adhesive integrity within a cured bondline of a bonded structural assembly, the system comprising:
    a bonded structural assembly having a cured bondline, the cured bondline comprising:
        an adhesive layer;
        a scrim ply layer integrated with the adhesive layer; and,
        an electrical sensor network integrated with the scrim ply layer, the electrical sensor network having sensor elements in the form of active sensor nodes integrated into the scrim ply layer and forming a network grid pattern across the scrim ply layer, and wherein the electrical sensor network comprises sensor elements having modalities based on ultrasonic wave propagation and electromechanical impedance;
    an electrical power source for providing electrical power to the electrical sensor network; and,
    a digital data communications network for retrieving and processing data from the electrical sensor network, wherein the electrical sensor network monitors adhesive integrity within the cured bondline on demand by interpreting changes in local dynamic responses and electromechanical properties directly measured within the cured bondline.

2. The system of claim 1, wherein the bonded structural assembly comprises a first structure made of a composite material, a metal material, or a combination thereof, bonded to a second structure made of a composite material, a metal material, or a combination thereof.

3. The system of claim 1, wherein the adhesive layer comprises a material selected from the group comprising epoxy adhesives, polyurethane adhesives, and toughened acrylic adhesives.

4. The system of claim 1, wherein the scrim ply layer comprises a material selected from the group comprising nylon fiber material, polyester fiber material, and glass fiber material.

5. The system of claim 1, wherein the scrim ply layer is multifunctional and acts as both an adhesive layer and a bondline monitoring system.

6. The system of claim 1, wherein the electrical sensor network comprises a plurality of spaced sensor elements selected from the group comprising active sensor nodes, separate sensing wires, separate sensing fibers, sensing fiber optic wires, sensing coatings on fibers, carbon nanotubes, and passive sensors.

7. The system of claim 6, wherein the sensor elements are integrated into a woven or random mat fiber layer of the scrim ply layer.

8. The system of claim 1, wherein the electrical power source and the digital data communications network are wireless.

9. The system of claim 1, wherein the local dynamic responses and electromechanical properties directly measured within the cured bondline are selected from the group comprising disbonds, weak bonds, strain levels, moisture ingression, materials change, cracks, voids, delamination, and porosity.

10. A system for monitoring adhesive integrity within a cured bondline of a bonded composite lamina assembly, the system comprising:
a bonded composite lamina assembly having a cured bondline, the cured bondline comprising:
an adhesive layer;
a scrim ply layer integrated with the adhesive layer; and,
an electrical sensor network integrated with the scrim ply layer, the electrical sensor network having sensor elements in the form of active sensor nodes integrated into the scrim ply layer and forming a network grid pattern across the scrim ply layer, and wherein the electrical sensor network comprises sensor elements having modalities based on ultrasonic wave propagation and electromechanical impedance;
a wireless electrical power source for providing electrical power to the electrical sensor network; and,
a wireless digital data communications network for retrieving and processing data from the electrical sensor network,
wherein the electrical sensor network monitors adhesive integrity on demand by interpreting changes in local dynamic responses and electromechanical properties directly measured within the cured bondline.

11. The system of claim 10, wherein the electrical sensor network comprises a plurality of spaced sensor elements selected from the group comprising active sensor nodes, separate sensing wires, separate sensing fibers, sensing fiber optic wires, sensing coatings on fibers, carbon nanotubes, and passive sensors.

12. The system of claim 11, wherein the sensor elements are integrated into a woven or random mat fiber layer of the scrim ply layer.

13. The system of claim 10, wherein the system is used for monitoring adhesive integrity within the cured bondline of the bonded composite lamina assembly in aircraft, spacecraft, aerospace vehicles, space launch vehicles, rockets, satellites, rotorcraft, watercraft, boats, trains, automobiles, trucks, buses, and architectural structures.

14. The system of claim 10, wherein the local dynamic responses and electromechanical properties directly measured within the cured bondline are selected from the group comprising disbonds, weak bonds, strain levels, moisture ingression, materials change, cracks, voids, delamination, and porosity.

15. A method for monitoring adhesive integrity within a cured bondline of a bonded structural assembly, the method comprising:
providing a bonded structural assembly having a cured bondline, the cured bondline comprising an adhesive layer, a scrim ply layer integrated with the adhesive layer, and an electrical sensor network integrated with the scrim ply layer, the electrical sensor network having sensor elements in the form of active sensor nodes integrated into the scrim ply layer and forming a network grid pattern across the scrim ply layer, and wherein the electrical sensor network comprises sensor elements having modalities based on ultrasonic wave propagation and electromechanical impedance;
activating the electrical sensor network to monitor adhesive integrity of the cured bondline on demand by interpreting changes in local dynamic responses and electromechanical properties directly measured within the cured bondline; and,
retrieving and processing adhesive integrity data of the cured bondline from the electrical sensor network via a digital data communications network.

16. The method of claim 15, wherein the electrical sensor network comprises a plurality of spaced sensor elements selected from the group comprising active sensor nodes, separate sensing wires, separate sensing fibers, sensing fiber optic wires, sensing coatings on fibers, carbon nanotubes, and passive sensors.

17. The system of claim 11, wherein the sensor elements are integrated into a woven or random mat fiber layer of the scrim ply layer.

18. The method of claim 15, wherein the method is used for monitoring adhesive integrity within the cured bondline of the bonded structural assembly in aircraft, spacecraft, aerospace vehicles, space launch vehicles, rockets, satellites, rotorcraft, watercraft, boats, trains, automobiles, trucks, buses, and architectural structures.

19. The method of claim 15, wherein the local dynamic responses and electromechanical properties directly measured within the cured bondline are selected from the group comprising disbonds, weak bonds, strain levels, moisture ingression, materials change, cracks, voids, delamination, and porosity.

20. The method of claim 15, wherein the digital data communications network is wireless.

* * * * *